(12) United States Patent
Brachman et al.

(10) Patent No.: US 10,888,710 B1
(45) Date of Patent: Jan. 12, 2021

(54) TRANSPARENT LOADING APPARATUS

(71) Applicant: GT Medical Technologies, Inc., Mesa, AZ (US)

(72) Inventors: David Brachman, Phoenix, AZ (US); Emad Youssef, Peoria, AZ (US); Peter Nakaji, Phoenix, AZ (US); Evan K. Fram, Phoenix, AZ (US)

(73) Assignee: GT MEDICAL TECHNOLOGIES, INC., Tempe, AZ (US)

( * ) Notice: Subject to any disclaimer, the term of this patent is extended or adjusted under 35 U.S.C. 154(b) by 339 days.

(21) Appl. No.: 15/824,182

(22) Filed: Nov. 28, 2017

Related U.S. Application Data (60) Provisional application No. 62/427,456, filed on Nov. 29, 2016.

(51) Int. Cl.
*A61N 5/10* (2006.01)

(52) U.S. Cl.
CPC ...... *A61N 5/1007* (2013.01); *A61N 2005/101* (2013.01); *A61N 2005/1009* (2013.01)

(58) Field of Classification Search
CPC ............ A61N 5/1007; A61N 2005/101; A61N 2005/1009
See application file for complete search history.

(56) References Cited

U.S. PATENT DOCUMENTS

| | | |
|---|---|---|
| D244,393 S | 5/1977 | Collica et al. |
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |

(Continued)

FOREIGN PATENT DOCUMENTS

| | | |
|---|---|---|
| BR | 11 2013 027841 2 | 4/2012 |
| CA | 2835065 | 2/2018 |

(Continued)

OTHER PUBLICATIONS

CivaSheet; "Precision Therapy Without the Beam"; CivaTech Oncology Inc.; CivaTech; https://civatechoncology.com/professionals/civasheet/2 pages; Accessed on Oct. 2018.

(Continued)

*Primary Examiner* — Kaylee R Wilson
(74) *Attorney, Agent, or Firm* — Knobbe, Martens, Olson & Bear LLP (57) ABSTRACT

A transparent loading apparatus (also referred to herein as a "loader") may partially or entirely comprise transparent material that allows light to pass through the loader and provides the viewer (whether manual or automated) a view of a radioactive seed, a seed carrier, a loading needle, etc. within the loader. In some embodiments, carrier material (e.g., collagen and/or other biocompatible material) and radioactive seeds (e.g., including a metal shielding and radioactive isotope) may transmit light to different degrees. For example, certain carriers, such as collagen carriers, may be translucent, while seeds may be opaque (or mostly opaque) to light. The systems discussed herein allow a viewer to detect location of a seed within a loader, and even within a carrier, because of these different light transmissivity characteristics.

10 Claims, 7 Drawing Sheets

(56) References Cited

U.S. PATENT DOCUMENTS

| | | |
|---|---|---|
| D381,080 S | 7/1997 | Ohata |
| 5,772,574 A | 6/1998 | Nanko |
| 5,803,895 A | 9/1998 | Kronholz et al. |
| 5,840,008 A | 11/1998 | Klein et al. |
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| 6,129,670 A | 10/2000 | Burdette et al. |
| D443,061 S | 5/2001 | Bergstrom et al. |
| 6,248,057 B1 | 6/2001 | Mavity et al. |
| 6,327,490 B1 | 12/2001 | Spetz |
| 6,358,195 B1 | 3/2002 | Green et al. |
| 6,360,116 B1 | 3/2002 | Jackson et al. |
| 6,385,477 B1 | 5/2002 | Werner et al. |
| 6,450,937 B1 | 9/2002 | Mercereau et al. |
| 6,471,631 B1 | 10/2002 | Slater et al. |
| 6,512,943 B1 | 1/2003 | Kelcz |
| 6,712,508 B2 | 3/2004 | Nilsson et al. |
| D488,864 S | 4/2004 | Fago et al. |
| 6,787,042 B2 | 9/2004 | Bond et al. |
| 7,011,619 B1 | 3/2006 | Lewis |
| D561,896 S | 2/2008 | Jones |
| D580,056 S | 11/2008 | Orthner |
| D580,057 S | 11/2008 | Ramadani |
| 7,776,310 B2 | 8/2010 | Kaplan |
| 8,039,790 B2 | 10/2011 | Cho et al. |
| D657,474 S | 4/2012 | Dona |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Eriksson |
| 8,605,966 B2 | 12/2013 | Eriksson |
| 8,825,136 B2 | 9/2014 | Giller et al. |
| 8,876,684 B1 | 11/2014 | Nakaji et al. |
| 8,939,881 B2 | 1/2015 | Nakaji et al. |
| 8,974,364 B1 | 3/2015 | Nakaji et al. |
| 9,022,915 B2 | 5/2015 | Nakaji et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 | 12/2016 | Brachman et al. |
| 9,545,525 B2 | 1/2017 | Nakaji et al. |
| 9,788,909 B2 | 10/2017 | Larkin et al. |
| 9,789,608 B2 | 10/2017 | Itkowitz et al. |
| 9,821,174 B1 | 11/2017 | Fram et al. |
| 10,080,909 B2 | 9/2018 | Brachman et al. |
| 10,085,699 B2 | 10/2018 | Brachman et al. |
| 10,265,542 B2 | 4/2019 | Brachman et al. |
| 10,350,431 B2 | 7/2019 | Nakaji et al. |
| 2001/0044567 A1 | 11/2001 | Zamora et al. |
| 2002/0058854 A1 | 5/2002 | Creed et al. |
| 2002/0120174 A1 | 8/2002 | Steele, Sr. et al. |
| 2003/0045769 A1 | 3/2003 | Kalas et al. |
| 2003/0088141 A1 | 5/2003 | Terwilliger et al. |
| 2003/0130573 A1 | 7/2003 | Yu et al. |
| 2003/0208096 A1 | 11/2003 | Tam |
| 2004/0109823 A1 | 6/2004 | Kaplan |
| 2004/0116767 A1 | 6/2004 | Lebovic et al. |
| 2004/0242953 A1 | 12/2004 | Good |
| 2005/0035310 A1 | 2/2005 | Drobnik et al. |
| 2005/0244045 A1 | 11/2005 | Eriksson |
| 2005/0267319 A1* | 12/2005 | White ................ A61N 5/1007 600/7 |
| 2006/0015030 A1 | 1/2006 | Poulin et al. |
| 2006/0063962 A1 | 3/2006 | Drobnik et al. |
| 2006/0173236 A1 | 8/2006 | White et al. |
| 2006/0235365 A1 | 10/2006 | Terwilliger |
| 2006/0253048 A1 | 11/2006 | Jones |
| 2007/0225544 A1 | 9/2007 | Vance et al. |
| 2008/0004714 A1 | 1/2008 | Lieberman |
| 2008/0009661 A1* | 1/2008 | Lamoureux ....... A61M 37/0069 600/7 |
| 2008/0146861 A1 | 6/2008 | Murphy et al. |
| 2008/0221384 A1 | 9/2008 | Chi Sing et al. |
| 2009/0012347 A1 | 1/2009 | Helle |
| 2009/0069625 A1* | 3/2009 | Helle ................ A61N 5/1007 600/7 |
| 2009/0131735 A1 | 5/2009 | Drobnik et al. |
| 2009/0156880 A1 | 6/2009 | Allan et al. |
| 2009/0253950 A1 | 10/2009 | Rapach et al. |
| 2009/0271715 A1 | 10/2009 | Tumuluri |
| 2010/0056908 A1 | 3/2010 | Giller et al. |
| 2010/0200778 A1 | 8/2010 | Drobnik et al. |
| 2010/0228074 A1 | 9/2010 | Drobnik et al. |
| 2010/0268015 A1 | 10/2010 | Drobnik et al. |
| 2010/0288916 A1 | 11/2010 | Cho et al. |
| 2010/0324353 A1 | 12/2010 | Helle |
| 2011/0013818 A1 | 1/2011 | Eriksson |
| 2011/0206252 A1 | 8/2011 | Eriksson |
| 2012/0165957 A1 | 6/2012 | Everland et al. |
| 2013/0102891 A1 | 4/2013 | Binnekamp et al. |
| 2013/0131434 A1 | 5/2013 | Nakaji et al. |
| 2013/0338423 A1 | 12/2013 | Nakaji et al. |
| 2014/0275715 A1 | 9/2014 | Brachman et al. |
| 2014/0296612 A1* | 10/2014 | Schwartz ........... A61N 5/1007 600/8 |
| 2014/0316187 A1 | 10/2014 | Nakaji et al. |
| 2015/0057487 A1 | 2/2015 | Nakaji et al. |
| 2015/0140535 A1 | 5/2015 | Geri et al. |
| 2015/0196778 A1 | 7/2015 | Nakaji et al. |
| 2015/0321024 A1 | 11/2015 | Nakaji et al. |
| 2015/0367144 A1 | 12/2015 | Flynn et al. |
| 2016/0242855 A1 | 8/2016 | Fichtinger et al. |
| 2017/0021191 A1 | 1/2017 | Brachman et al. |
| 2017/0120073 A1 | 5/2017 | Brachman et al. |
| 2017/0215824 A1 | 8/2017 | Brachman et al. |
| 2017/0252575 A1 | 9/2017 | Nakaji et al. |
| 2020/0047001 A1 | 2/2020 | Nakaji et al. |

FOREIGN PATENT DOCUMENTS

| | | |
|---|---|---|
| CA | 2834559 | 11/2018 |
| CA | 3017174 | 1/2020 |
| DE | 613 528 | 5/1935 |
| EP | 0 292 630 B1 | 8/1995 |
| EP | 0 906 769 A2 | 4/1999 |
| EP | 2701803 B1 | 8/2018 |
| EP | 3456384 | 3/2019 |
| JP | S52-9424 | 7/1975 |
| JP | H09-028810 | 4/1997 |
| JP | 2001-266903 | 9/2001 |
| JP | 3095304 | 7/2003 |
| JP | 2007-512112 | 5/2007 |
| JP | 2009-515603 | 4/2009 |
| JP | 2010-536529 | 12/2010 |
| JP | 6365983 | 7/2018 |
| WO | WO 2007/106531 A1 | 9/2007 |
| WO | WO 2012/100206 A2 | 7/2012 |
| WO | WO 2012/149580 A1 | 11/2012 |
| WO | WO 2016/171961 | 10/2016 |
| WO | WO 2016/179420 | 11/2016 |

OTHER PUBLICATIONS

CivaSheet; "Precision Therapy Without the Beam"; CivaTech Oncology Inc.; CivaTech; https://civatechoncology.com/products-2/products/; 5 pages; Accessed on Oct. 2018.

(56) References Cited

OTHER PUBLICATIONS

Aima, Manik et al.; "Dosimetric Characterization of a New Directional Low-Dose Rate Brachytherapy Source"; Department of Medical Physics; Mar. 11, 2018; 32 pages.
Rivard, Mark J.; "A Directional Pd Brachytherapy Device: Dosimetric Characterization and Practical Aspects for Clinical Use"; Department of Radiation Oncology; Brachytherapy 16 (2017) pp. 421-432.
Office Action dated Nov. 2, 2017; European Patent Application No. 12724427.5; 4 pages.
Extended European Search Report; Application No. 18186392.9; dated Jan. 7, 2019; 7 pages.
Cole, P.D., et al., "A comparative long-term assessment of four soft tissue supplements". Anesthetic Surg J. 31(6). 674-681, 2011.
International Search Report; International Application No. PCT/US2012/035907, dated Sep. 26, 2012; 3 pages.
International Search Report; International Application No. PCT/US2012/035909, dated Aug. 30, 2012; 3 pages.
Crepeau, R.H., et al., "Image Processing of Imperfect Protein Arrays: Sectioned Crystals and Tubulin Sheets and Rings". Elec. Microsc. Soc. Amer. Proc. 40:84-87, 1982.
Crepeau, R.H., et al., "Reconstruction of imperfectly ordered zinc-induced tubulin sheets using cross-correlation and real space averaging". Ultramicroscopy, 6, 7-18, 1981.
Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.
Delaney, T.F., et al., "Intraoperative dural irradiation by customized 192I iridium and 90 Yttrium brachytherapy plaques". Int. J. Radiat Oncol Biol Phys. 57(1): 239-245, 2003.
Ewersten, et al., "Biopsy Guided by Real-Time Sonography Fused with MRI: A Phantom Study", American Journal of Roentgenology. 2008; 190: 1672-1674. 10.2214/AJR.07.2587.
Gutin, P.H., et al., "A coaxial catheter system for afterloading radioactive sources for the interstitial irradiation of brain tumors. Technical note". J. Neurosurg 56: 734-735, 1982.
Gutin, P.H., et al., "Brachytherapy of recurrent tumors of the skull base and spine with iodine-125 sources". Neurosurgery 20:938-945, 1987.
Hamilton, A.J., et al., "The use of gold foil wrapping for radiation protection of the spinal cord for recurrent tumor therapy". Int. J. Radiat Oncol Biol Phys. 32(2):507-511, 1995.
Hilaris, B.S., et al., "Interstitial irradiation for unresectable carcinoma of the lung". Ann Thoracic Surg; 20:491-500, 1975.
Hilaris, B.S., et al., "Intraoperative radiotherapy in stage I and II lung cancer". Semin Surg Oncol. 3:22-32, 1987.
Huang, K., et al., "Surgical resection and permanent iodine-125 brachytherapy for brain metastases". J. Neurooncol. 91:83-93, 2009.
Jenkins, H.P., et al., "Clinical and experimental observations on the use of a gelatin sponge or foam". Surg 20:124-132, 1946.

Kneschaurek, P. et al.: "Die Flabmethode Zur Intraoperativen Bestrahlung. Öthe Flab-Method for Intraoperative Radiation Therapy", Strahlentherapie and Oknologie, Urban Und Vogel, Muenchen, DE, vol. 171, No. 2; Feb. 1, 1995, pp. 61-69, XP000610565, ISSN:0179-7158.
Marchese, M.J., et al., "A versatile permanent planar implant technique utilizing iodine-125 seeds imbedded in gelfoam". Int J Radiat Oncol Biol Phys 10:747-751, 1984.
Murphy, M.K., et al., "Evaluation of the new cesium-131 seed for use in low-energy x-ray brachytherapy". Med Phy 31(6): 1529-1538, Jun. 2004.
Nori, D., et al., "Intraoperative brachytherapy using Gelfoam radioactive plaque implants for resected stage III non-small-cell lung cancer with positive margin: A pilot study". J Surg Oncol. 60:257-261, 1995.
Parashar, B., et al., "Cesium-131 permanent seed brachytherapy: Dosimetric evaluation and radiation exposure to surgeons, radiation oncologists, and staff". Brachytherapy. 10:508-511, 2011.
Patel, S., et al., "Permanent iodine-125 interstitial implants for the treatment of recurrent Glioblastoma Multiforme". Neurosurgery 46 (5) 1123-1128, 2000.
Rivard, M.J., "Brachytherapy dosimetry parameters calculated for a 131 Cs source". Med Phys. 34(2): 754-765, 2007.
Rogers, C.L., et al., "Surgery and permanent 125-1 seed paraspinal brachytherapy for malignant tumors with spinal cord compression". Int. J. Radial Oncol Biol Phys. 54(2): 505-513, 2002.
Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.
Office Action dated Apr. 2, 2015; European Patent Application No. 12724426.7; 5 pages.
Office Action dated Oct. 30, 2015; European Patent Application No. 12724426.7; 4 pages.
Office Action dated Feb. 9, 2016; Japanese Application No. 2014-508190; 5 pages including english translation.
International Search Report; International Application No. PCT/US2016/031035; filed May 5, 2016; 15 pages.
International Search Report and Written Opinion; International Application No. PCT/US2016/027143, filed Apr. 12, 2016; dated Aug. 25, 2016; 7 pages.
Decision of Rejection dated Feb. 4, 2016, Japanese Patent Application No. 2014-508190 with English Translation; 4 pages.
Search and Examination Report; Application No. P1140/13; filed Oct. 24, 2013 (PCT Apr. 30, 2012); 10 pages.
Summons to Attend Oral Proceedings dated Aug. 18, 2017; European Application No. 12724426.7; 5 pages.
Miller, S., et al., "Advances in the virtual reality interstitial brachytherapy system." Engineering Solutions for the Next Millenium. 1999 IEEE Canadian Conference on Electrical and Computer Engineering (Cat. No. 99TH8411). vol. 1. IEEE, 1999.

* cited by examiner

TRANSPARENT LOADING APPARATUS

PRIORITY CLAIM

This application is a non-provisional of and claims priority to U.S. Provisional Patent Application No. 62/427,456, filed Nov. 29, 2016, entitled "TRANSPARENT LOADING APPARATUS." The disclosure of the foregoing application is hereby incorporated by reference in its entirety.

FIELD

The invention generally relates to improvements to radioactive brachytherapy.

BACKGROUND

Tumors in living organisms are highly variable in size, location and their amount of infiltration into normal tissues, and the variability of tumors in general make them very difficult to treat with a one-size fits all approach. Furthermore, the extent of tumors and/or void created upon debulking are typically not known until presented in the operating room. Thus, the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, such as when treating gynecologic malignancies; intraluminal, such as when treating esophageal or lung cancers; external surface, such as when treating cancers of the skin, or interstitial, such as when treating various central nervous system tumors as well as extracranial tumors of the head and neck, lung, soft tissue, gynecologic sites, liver, prostate, and skin.

SUMMARY

The systems, methods, and devices described herein each have several aspects, no single one of which is solely responsible for its desirable attributes. Without limiting the scope of this disclosure, several non-limiting features will now be described briefly.

As discussed herein, a transparent loading apparatus (also referred to herein as a "loader") may comprise transparent material that allows light to pass through the loader and provides the viewer (whether manual or automated) a view of a seed carrier, radioactive seed, loading needle, etc. within the loading apparatus. In some embodiments, carrier material (e.g., collagen and/or other biocompatible material) and radioactive seeds (e.g., including a metal shielding and radioactive isotope) may transmit light to different degrees. For example, certain carriers, such as collagen carriers, may be translucent, while seeds may be opaque (or mostly opaque) to light. The systems discussed herein allow a viewer to detect location of a seed within a loader and even within a carrier because of these different light transmissivity characteristics.

BRIEF DESCRIPTION OF THE DRAWINGS

The principles of the present invention will be apparent with reference to the following drawings, in which like reference numerals denote like components:

FIG. 4 includes FIGS. 4A, 4B and 4C wherein

DETAILED DESCRIPTION

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Various embodiments of the loading apparatus are discussed herein, and any such embodiments may include one or more (up to all) surfaces that are transparent (or at least partially transparent). A "surface" generally refers to a substrate, e.g., an entire thickness of a top surface, but may refer to only a portion of a thickness of a substrate (e.g., a portion of a thickness of a top surface). Thus, if a particular loader includes a top surface, bottom surface, front surface, and end surface, any one or more of these surfaces may be transparent. For example, in one embodiment only the top surface and bottom surface are transparent, while in another embodiment each of the four surfaces are transparent. Advantageously, such transparent surfaces allow the viewer to know the seed position while it is still being positioned within the loader and, importantly, within the seed carrier. Thus, the seed may be positioned more precisely within the seed carrier. As used herein, the term "transparent" generally refers to the material that is at least partially transparent, which includes surfaces that are at least partially opaque also including surfaces that are not opaque. In some embodiments, a level of transparency is determined to be high enough to allow a human viewer and/or viewing apparatus (e.g., an imaging device) to detect position of the radioactive seed within the loader and, in some embodiments, within the seed carrier (e.g., the biocompatible material, such as collagen).

Definitions

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Tumor: an abnormal growth of tissue resulting from uncontrolled, progressive multiplication of cells. Tumors can be benign or malignant.

Tumor bed: an anatomical area of a patient (e.g., a human or other mammal) where a tumor exists (pre-operative tumor bed) and/or an area surrounding a surgically removed tumor (post-operative tumor bed), such as a cranial cavity from which a tumor was surgically removed. Even after surgical removal of a tumor, the remaining tumor bed of the patient may include tumor cells.

Treatment area: an anatomical area that is targeted for delivery of radiation, such as from one or more radiation delivery devices (e.g., the carriers discussed below). A treatment area may include tissue below and/or around a location where the radiation deliver device is positioned, such as an anatomical area of a tumor or a tumor bed.

Treatment surface: an anatomical surface of a patient where a radiation delivery device is to be placed to deliver radiation to a treatment area, such as the treatment surface itself and/or tissue below the treatment surface. A treatment surface may be a portion of a tumor bed or any other anatomical surface. For example, if a tumor bed is surgically created, the treatment surface may include an entire exposed surface of the tumor bed, a portion of such exposed surface, or the entire exposed surface of the tumor bed as well as a surrounding area of tissue.

Brachytherapy: radiation treatment in which the radiation delivery device is placed directly on and/or close to a treatment surface of the body, such as directly on the surface of the body, within the body, or in a tumor bed. For example, brachytherapy may be intracavitary, such as in cranial or gynecologic malignancies; intraluminal, such as in esophageal or lung cancers; external, such as in cancers of the skin; and/or interstitial, such as in treatment of various central nervous system tumors as well as extracranial tumors of the head, neck, lung, soft tissue, gynecologic sites, rectum, liver, prostate, and penis.

Seed: a radioactive material that is configured for delivery of radiation to a tumor and/or tumor bed. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more of multiple radioactive components, such as Cs 131, Ir 192, I 125, Pd 103, for example. Seeds may include a protective outer shell that partially or fully encases the radioactive material. Seeds are one form of radiation source. The term "radiation source," as used herein, generally refers to a radioactive seed (or other object that emits radiation), either alone (e.g., a seed) or embedded, or otherwise attached to, a carrier (e.g., a tile carrier with an embedded radioactive seed).

Carrier: a substrate that holds or contains a radioactive seed. A carrier that contains one or more seeds is a radiation delivery device. Carriers may comprise various materials, such as one or more biocompatible materials including collagen. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes. Examples carriers, such as carriers having various sizes, shapes, configurations, etc., are included in the following patent and patent application, each of which is hereby incorporated by reference in its entirety and for all purposes:

U.S. patent application Ser. No. 14/322,785, filed Jul. 2, 2014, now U.S. Pat. No. 8,876,684, entitled "Dosimetrically Customizable Brachytherapy Carriers and Methods Thereof In The Treatment Of Tumors," and U.S. patent application Ser. No. 14/216,723, filed Mar. 17, 2014, publication No. 2014/0275715, entitled "Dosimetrically Customizable Brachytherapy Carriers and Methods Thereof In The Treatment Of Tumors."

Tile Carrier (also referred to as "Tile"): type of carrier that is substantially planar and generally maintains a two-dimensional planar geometry when placed in a tumor bed. Depending on the material of the tile, though, the tile may be malleable such that the tile can be deformed by bending in order to better conform to a tumor bed. For example, for tiles comprising essentially collagen (and/or other malleable materials), the tiles may be substantially bent as placed in or on a treatment surface (and/or when pressed against the treatment surface) to conform with the shape of the treatment surface, such as a post-operative tumor bed.

Gore Carrier (also referred to as "Gore"): type of carrier that is 3-dimensional and conforms to the tumor bed while maintaining the geometry necessary for an effective implant. In some embodiments, gores are initially planar and are reconfigured to take on a 3-dimensional shape, such as to form a hemispherical surface that may be placed into a similarly shaped tumor cavity.

Star Carrier (also referred to as "Star" or "arm-based carrier"): type of carrier that assumes a conformable 3-dimensional shape when arranged and placed into an operative cavity or similar space and conforms to the treatment environment while maintaining the geometry necessary for an effective implant. However, in some embodiments, Star carriers may be used in their initial planar state to cover a relatively flat tumor or tumor bed area.

Loader: a device that aids in placement of radioactive seeds in carriers, such as via injection of seeds into carriers. A loader, also referred to herein as a "loading device," may include multiple components, such as to hold a carrier in place and guide a delivery device (e.g., a needle or injector) into the carrier in order to place a seed at a precise location in the carrier. U.S. patent application Ser. No. 13/460,809, filed Apr. 30, 2012, now U.S. Pat. No. 8,939,881, entitled "Apparatus For Loading Dosimetrically Customizable Brachytherapy Carriers," and U.S. patent application Ser. No. 14/696,293, filed Apr. 24, 2015, entitled "Apparatus and Method for Loading Radioactive Seeds Into Carriers," which are each hereby incorporated by reference in their entirety for all purposes, describe several embodiments of loaders. As discussed further herein, loaders may be operated manually, such as by human operators, or may be fully automated, such that carriers can be loaded with seeds using an automated process. Alternatively, loaders may be configured to be automated in part and require manual operation in part.

Shielding Material: any material that restricts movement of radioactive particles, such as by absorbing, reflecting, and/or scattering radioactive particles. The term "shielding," as used herein, generally refers to any mechanism of preventing radiation from moving through and exiting a corresponding shielding material, such as by the shielding material absorbing, reflecting, or otherwise blocking the radiation. Shielding materials in various forms may be used in the various embodiments discussed herein. For example, a shielding material may be in the form of a particle, wire, rod, cylinder, bar, sheet, liquid, solution, foam, or any other form in which a material having radiation absorbing and/or reflecting properties is possible. A shielding material provides a shielding rate, which is generally an amount of shielding of radioactive energy (that is emitted from one or more radiation sources), provided by the particular shielding materials. Similarly, a shielding layer comprising multiple shielding materials and an isolation sheet have associated shielding rates, which are dependent on the combination of shielding (and possibly non-shielding) materials therein. For some applications, such as based on clinical need, an isolation sheet that provides a shielding rate of 25%, 50%, 75%, 90%, 95%, 98%, or some other shielding percentage, may be desired. As discussed herein, material composition, shape, size, dimensions, etc. may impact the shielding abilities of a shielding material. For applications (e.g., based on clinical need) where a higher shielding percentage is desired than may be provided by a single shielding material, multiple shielding materials may be used in combination, in one or more shielding layers or isolation sheets.

In some embodiments, shielding materials comprise high Z materials, such as tantalum, gold, platinum, tin, steel, copper, aluminum, etc. (e.g., a 0.05 mm to 0.2 mm thickness metallic foil). In other embodiments, any other material that reduces penetration of radiation may be a shielding material. For example, a non-metallic, yet dense compound, may be used alone (or in combination with a metallic material) as a shielding material. Such a non-metallic shielding material may advantageously lessen the chance of 1) MRI artifacts, 2) deflection of the isolation sheet, and/or 3) MRI-induced heating, such as may be caused by current loop induction and/or radio-frequency induced tissue heating that may be caused by metallic shielding materials. Depending on the particular non-metallic material, thickness of the material may be larger than a required thickness of a metallic shielding material, in view of the general enhanced shielding abilities of metallic materials. Non-metallic high density shielding materials may beneficially provide shielding of non-target tissues from radiation particularly in applications where MRI or other magnetic field exposure may be anticipated. Examples of non-metallic shielding materials include polyetheretherketone (PEEK), nanoparticles, polymeric nanoparticles, encapsulated nanoparticles, calcium carbonate, calcium phosphate, calcium sulfate, barium sulfate, zirconium dioxide, polymers and polymer hybrids of these and other materials. Shielding materials may be combined to form a composite shielding material. For example, a metallic cylinder may be filled with (non-metallic) liquid calcium carbonate, in order to form a shielding material that better addresses one or more of the clinical needs of the patient than a separate metallic cylinder and liquid calcium carbonate or a solid metallic rod.

High Z Materials: any element with an atomic number greater than 20, or an alloy containing such materials.

Teletherapy generally refers to radiation treatment in which the source of the radiation is at a distance from the body.

High Dose Rate generally refers to treatment with radiation doses above 12,000 cGy/hr.

Low Dose Rate generally refers to treatment with radiation in the dose range of 400-2000 cGy/hr.

Hot generally refers to a material that is Radioactive, while Cold generally refers to a material that having no or low in radioactivity.

Dosimetry generally refers to the process of measurement and quantitative description of the radiation absorbed dose (rad) in a tissue or organ.

Transparent generally refers to a characteristic of a material that allows light to pass through the material such at least some of the light is visible by a human (e.g., visible light) and/or detectable by a machine (e.g., infrared light). A transparent material is at least partially transparent. Thus, some transparent surfaces are partially opaque, while others are not opaque at all. In some embodiments, a level of transparency is determined to be high enough to allow a human viewer and/or viewing apparatus (e.g., an imaging device) to detect position of a radioactive seed within the loader and, in some embodiments, within a seed carrier (e.g., the biocompatible material, such as collagen) positioned in the loader.

Carrier Systems

Figure 6:
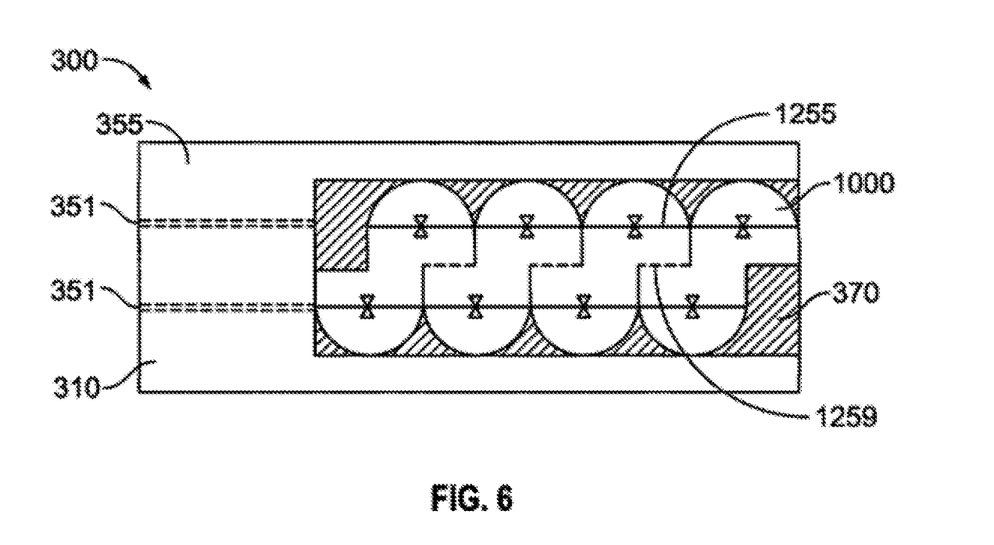
FIG. 6 is a top plan view of a radioactive carrier positioned in the loading bed of a loading device.
Figure 7:
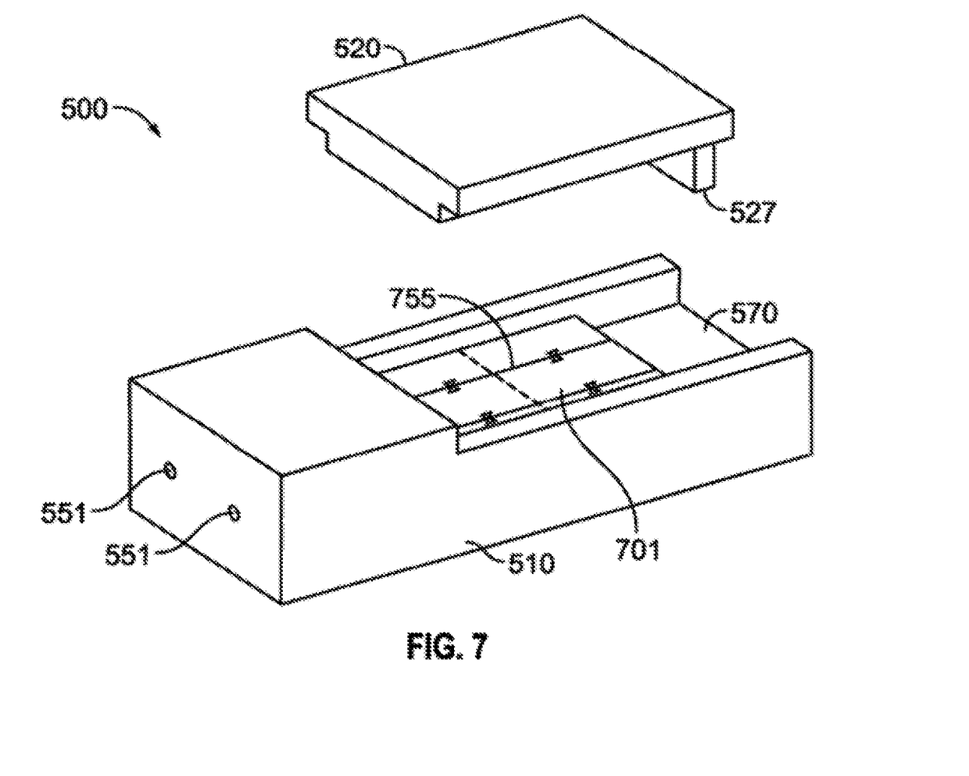
FIG. 7 is a perspective view of a tile carrier positioned in the loading bed of a loading device.

Generally the carrier systems described herein involve the utilization of small individual implantable carriers in the form of gores (e.g., gore carrier 1000 in a loader 300 in FIG. 6) and tiles (e.g., tiles 701 illustrated in a loader 500 in FIG. 7). Carriers are designed to be bearers of therapeutic agents such as radioactive seeds to produce a dosimetrically customizable implant in real time for each patient and tumor.

The carrier systems are designed to create a carrier which allows for more precise and stable dosimetry; an improved geometry with a better orientation of seeds to one another especially in the settings of real-time, intraoperative environments; are fully customizable to size/volume, location, and tumor type; and/or can provide differential dosing of tumor/tumor bed vs. normal tissues.

Loading Devices

FIGS. 1-8 demonstrate various embodiments of specialized loader systems for loading carriers with radioactive seeds. The loaders of the present invention may be used with the carriers either to create prepackaged hot carriers or to load "cold" carriers just prior to use.

The embodied loaders can be single or multi-use, sterilizable, and shielded if desired. They are designed to load either standard or high-Z material carriers in an accurate, efficient, and real-time manner. The loaders are of similar designs, dimensionally specific, and each comprises at least two components, the base and the lid.

The loader designs of the present invention can be made to accommodate a wide variety of carrier dimensions and styles. They are illustrated to accommodate seed-in-suture, but can be easily adapted for loose seeds or other configurations.

When loading a seed in suture a needle longer than the loader may be used and pulled through the loader channel holes on the proximal end of the base and the distal of the lid. Once the needle protrudes it may be pulled the rest of the way with clamps, needle-nose plier, or another tool (such as an automated robotic tool). One example is wherein you have a 60 mm loader you may want to use a 70 mm (or longer) needle to feed through the loader channels and deposit the seeds within the carrier.

Example Tile Loader System

In one embodiment, a loader comprises a sterilizable single or multi-use device for manual or automated loading (in real time or for pre-loading) of carriers such as but not limited to tiles, gores, or stars with radioactive seeds such as $I^{125}$, $Cs^{131}$, $Pd^{111}$, $Pd^{103}$ and/or other materials. The loaders may be constructed of metal, plastic or composite material, and manufactured by casting, molding, stamping, forming or 3D printing. Embodiments of the loaders contemplated may include shielding either by way of construction with a high Z material, or with other materials with a sufficient dimension (thickness) to provide the necessary dose attenuation for a user.

Alternative embodiments may remain unshielded, and be made of materials suitable for the purpose including but not limited to tungsten, stainless steel, nylon or plastic.

The embodied Loader device generally has two components, a base and a lid. But each component has multiple and specialized functions when used to load radionuclide carriers. In some embodiments, loaders may include only the top and bottom surface, such as planar surfaces, that engage with a carrier while a CD is implanted within the carrier. For example, an automated system may include one or more automated movable surfaces, such as a top plate that moves up and down using hydraulic, electronic, or manual energy, to selectively engage a carrier that is placed on a lower surface.

In some embodiments, loaders comprise a base or "bed" that defines a space into which a preformed radionuclide or brachytherapy carrier (e.g., a tile, gore, star, or other carrier) is placed. This bed area is of a fixed dimension specific to the loader, and loaders are contemplated in multiple sizes identified for this purpose by the bed size. Bed sizes contemplated may be almost any dimension, such as between 1 cm×1 cm to 4 cm×4 cm (for example 1×2 cm, 2×3 cm and 3×4 cm). In some embodiments, bed sizes are even larger, such as 5×5 cm, 10×10 cm, or larger.

The base of the loaders function to: 1) guide the initial path of the loading needle for seed placement in the carrier; 2) provide dimensional stability to the soft carrier during the loading process; 3) center the carrier left-right within the base during the loading process; and 4) shield the user.

The "structure" of the base comprises a portion with an internal tunnel of appropriate length and diameter (e.g. 20 mm×1.2 mm) which guides the initial path of the loading needle for accurate seed placement in the carrier; and 2) sufficient material to constrain the carrier in the bed on 4 sides with; 3) exterior dimensions which may vary with the material/construction materials used; and 4) the need for a shielded or unshielded device.

Figure 1:
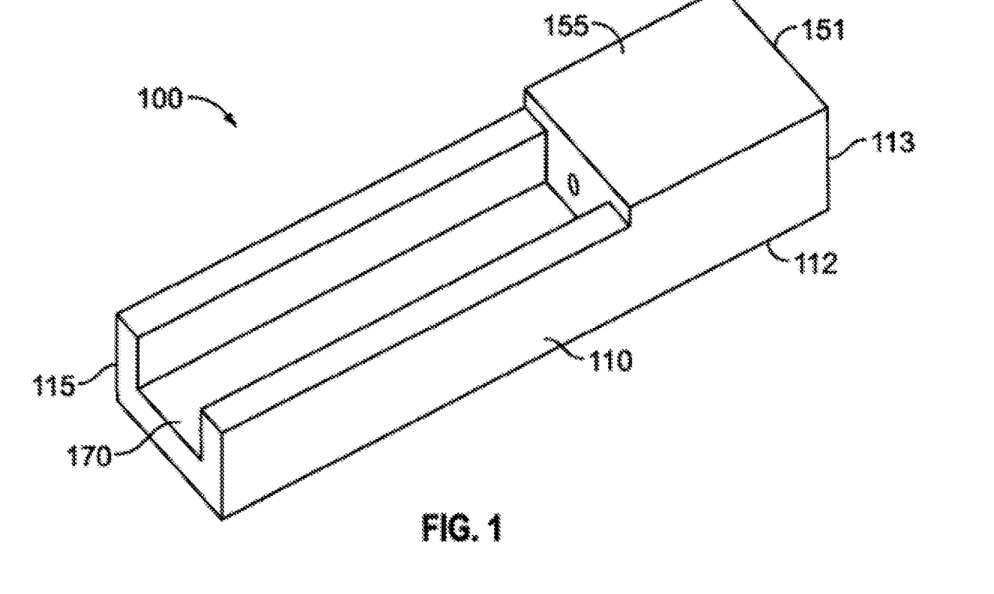
FIG. 1 is a diagram of an example loading device (or "loader")

An exemplary base of a loader device 100 is shown in FIG. 1, the base 110 has a bottom surface 112 a top surface 114, a proximal end 113, a distal end 115. A radionuclide loading entry channel 151 is located on the proximal end 113 of the base 110 and a loading support channel 155 begins at the loading entry channel 151 and extends through the base 110 until reaching the loading bed 170. The loading bed 170 extends from the end of the support channel 155 until the distal end 115 of the base 110.

In some embodiments, loaders include a lid that may be configured to: 1) guide the final path of the loading needle, entirely through the carrier; 2) provide dimensional stability to the soft carrier during the loading process; 3) position the carrier superior-inferiorly within the base during the loading process; 4) position the carrier front to back within the base during the loading process; and/or 5) shield the user.

An additional aspect of the lid may be to function as a guide for the terminal path of the loading needle through the specific placement of an opening along its far aspect to accept the tip of the loading needle and thereby assure accurate placement of the seeds. Lids is conceived of as being made of as a set for each standard base so that, as an example, a 1×4 cm base can be used to load a 1×2 cm, 1×3 cm, or 1×4 cm carrier by utilizing a lid of appropriate length.

A further feature of this design is that there is a "tooth" on the end of the less than full length lids which add further stability when loading shorter length carriers.

Figure 2:
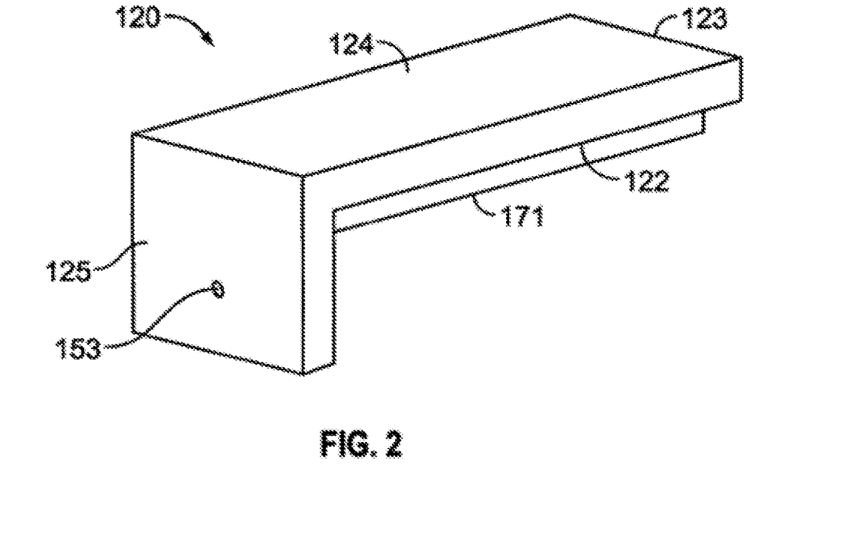
FIG. 2 is a diagram of an example lid that may be used in conjunction with the loader of FIG. 1 and/or other loaders.

An exemplary lid of a loader device 100 is shown in FIG. 2, the lid 120 has a bottom surface 122 a top surface 124, a proximal end 123, a distal end 125. A radionuclide loading exit channel 153 is located on the distal end 125 of the lid 120. A loading bed insert 171 is located on the bottom surface 122 of the lid 120 and is configured to have dimensions that mate with the loading bed 170 of the base.

Figure 3:
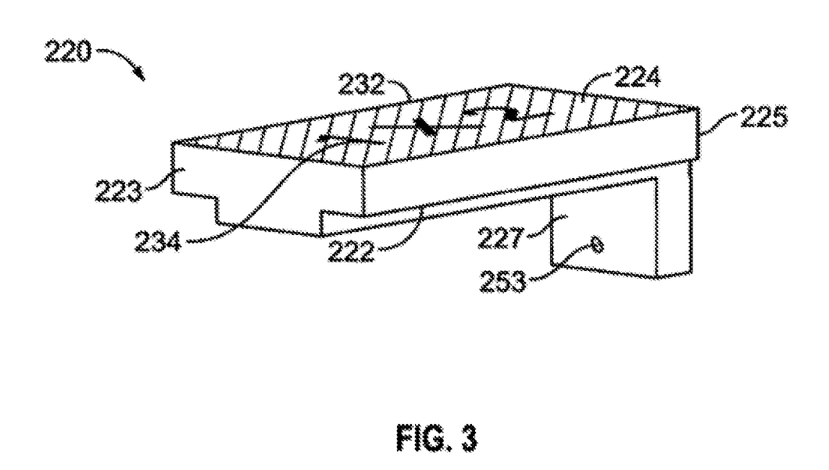
FIG. 3 is a diagram of another example lid that may be used in conjunction with the loader of FIG. 1 and/or other loaders.

FIG. 3 illustrates another embodied lid 220 with a bottom surface 222 a top surface 224 which has real time visual enhancement features 234 to help assist the user in the operating field to determine the correct properties of the loader being used. In this case the visual enhancement features are stamped dimensions 234. The top surface 224 also has an external texture feature 232 which assists the user with handling the loader 200 in an operating field setting. In applications where the distance from the proximal end 223, to the distal end 225 of a lid 220 is less than the length of the loading bed 170 the lid 220 is designed to mate with the loading bed 270 so a tooth feature 227 is present on the distal end 225 of the lid 220. The tooth 227 mates with the loading bed 270 at a dosimetrically advantageous place in order to create a smaller loading cavity and provide structural support for a shorter radionuclide carrier. The exit channel 253 extends through the tooth 227 and out of the device 200.

Figure 4A:
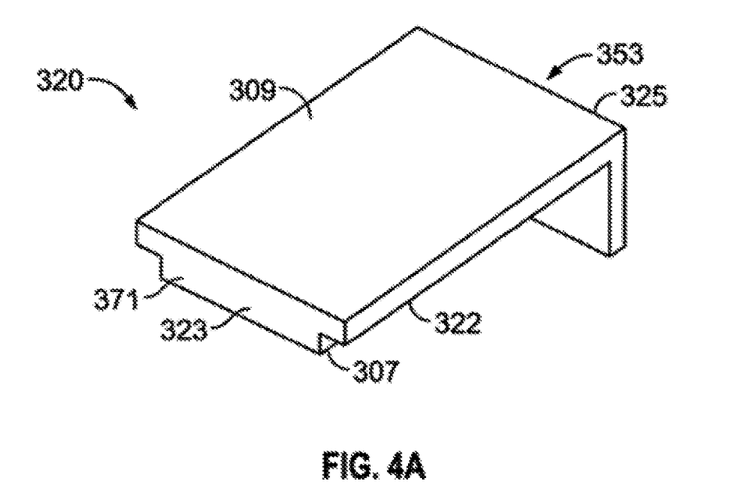
FIG. 4A shows a perspective view of a lid configured for engagement with a the loading device of FIG. 4B.
Figure 4B:
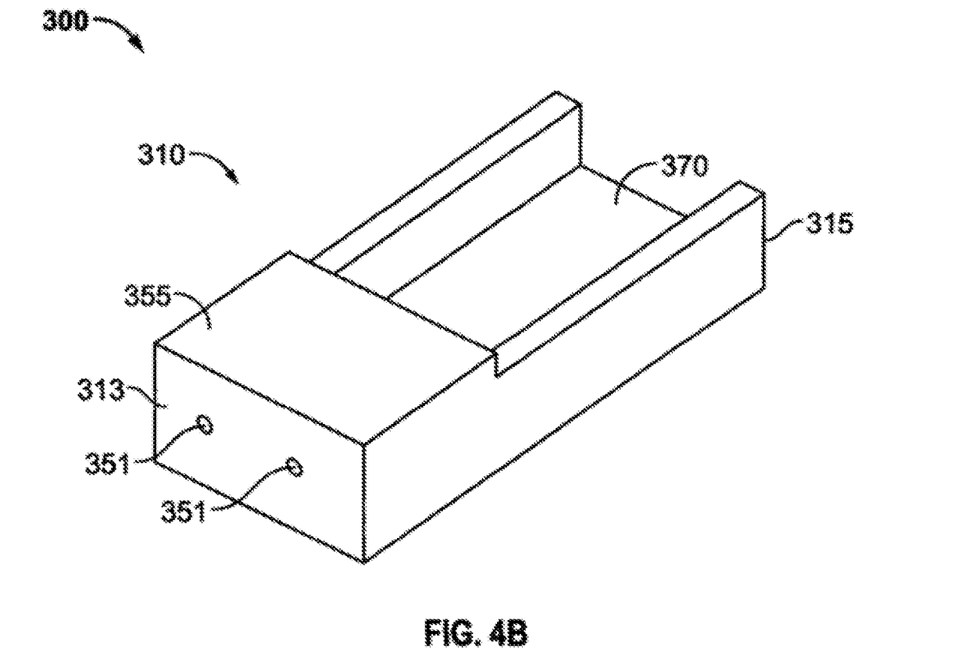
FIG. 4C illustrates the example lid of FIG. 4A engagement with the example loading device of FIG. 4B.
Figure 4C:
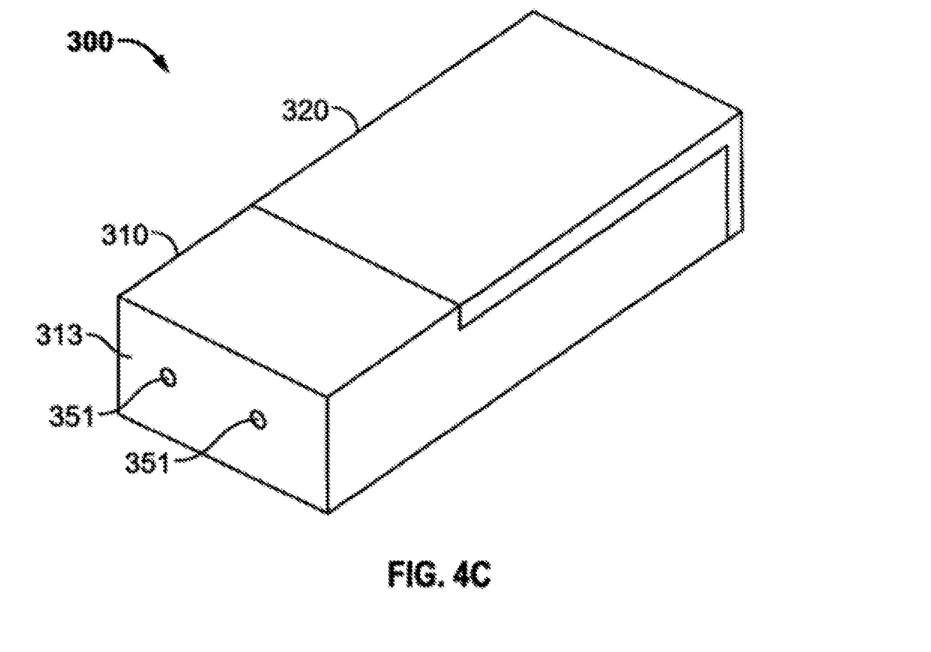

FIG. 4 includes FIGS. 4A, 4B and 4C wherein FIG. 4A shows a perspective view of a lid 320 to an embodied loading device 300; FIG. 4B shows a perspective view of the base 310 of an embodied loading device 300; and FIG. 4C shows a perspective view of an embodied loading device 300 with the lid 320 in its secured position on the base 310. The lid 320 has a bottom surface 322 and a top surface 324 a proximal end 323 and a distal end 325 and a loading bed insert 371 located on the bottom surface 322 and running from the proximal end 323 to the distal end 325. Additionally, there are loading channel exit holes 353 (not visible in the angle of FIG. 4A) extending through the distal end 3025 of the lid. The base 310 as shown in FIG. 4B comprises of the proximal end 313 and a distal end 315 a proximal end loading channel 351 and a loading channel support structure 355 which provides enough depth to guide a needle in a consistent and accurate pathway as the needle tip travels through any loading material if present, and exits out a loading channel exit hole 353. Additionally, the loader 300 comprises a loading bed 370 in which appropriately sized carrier material is placed to be loaded. Once a carrier is placed into the loading bed 370 to be loaded the lid 320 is placed onto the base 310, as shown in FIG. 4C, such that the loading bed insert 371 located on the bottom surface 322 of the lid 320 engages with the loading bed 370 portion of the base 310. The depth of the loading bed insert 371 is chosen so that it is deep enough to sandwich the carrier material in place during the process of loading but not too much depth which crushes the carrier and repulses the ability of the loading needle to extend through a loading channel 351.

Figure 5:
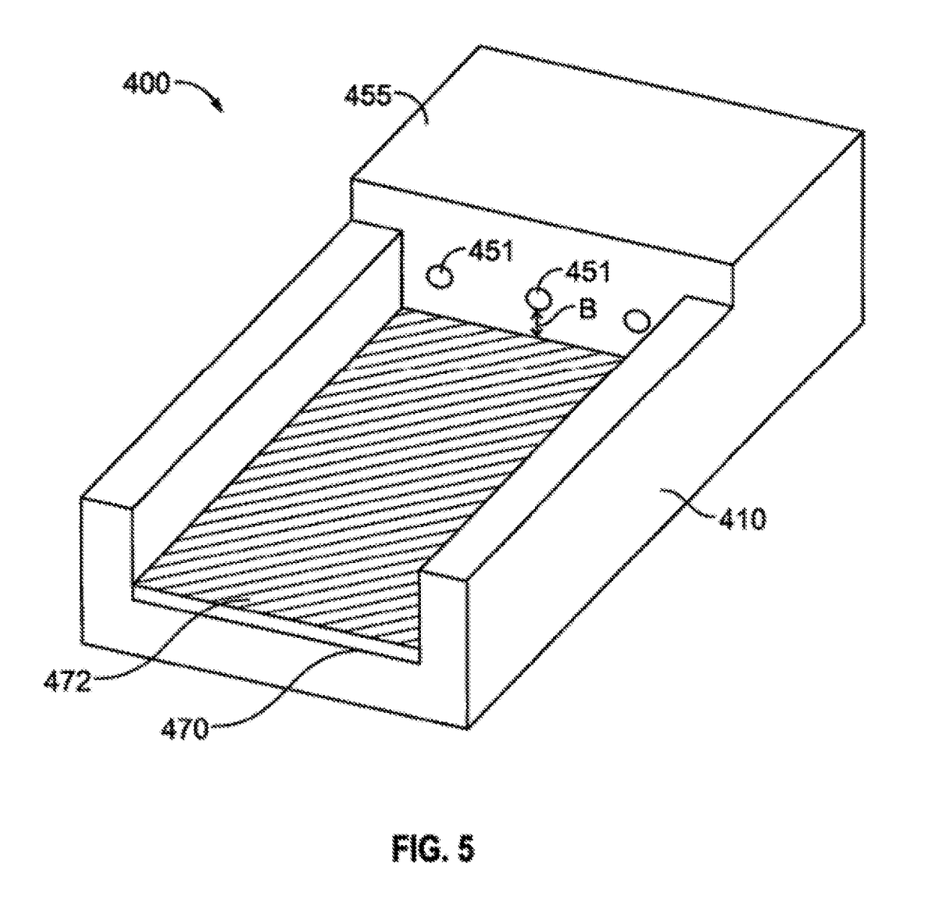
FIG. 5 is a diagram of another example loader.

Another loading device which allows for variable customization is shown in FIG. 5. The loader shown in this embodiment displays the variable distance possibilities between the loader bed 470 and the loading entry channels 451 and is measured as distance "b". This "b-value" can be made shorter by adding one or more bed-liners 472 placed into the bed 470 of the loader 400. The bed liners can be as thin as 0.5 mm (or smaller) and as thick as 2.0 mm (or larger), with 0.75 to 1.5 mm preferred and 1 mm most preferred. This "b"-value variation can be used to provide various loading arrangements which allows the user to create a carrier with customized but variable depths of carrier material and allows for more precise and predictable real-time dosimetry in the operating field.

In some embodiments, bed liners may include scorings, markings, or other indicators that provide information to the user as to the location of a carrier and/or seed(s) on the loader. For example, utility of a loader may be modified to enable quality control of seeds already placed in a carrier using such a bed liner, either in realtime as the seeds are being placed and/or as part of a quality assurance process. For example, a bed liner insert (placed in a loader) with markings at 0.8 cm, 1.0 cm or 1.2 cm on center would allow the manufacture or quality assurance monitoring of various seed placements (such as seeds that were previously placed in the same or a separate loader). Depending on the embodiment, these bed liners, as well as the bed, may include at least a portion that is at least partially transparent.

FIG. 6 is a top plan view of an embodied gore carrier 1000 shown when placed in the loading bed 370 of loader device 300. FIG. 6 shows the gore 1000 placed within the loading bed 370 portion of the loader 300. The lid 320 portion of the loader has been removed so that the gore 1000 is visible and one can see that the orientation lines 1255 of the gore I 000 align directly with the loading channel support structure 355 such that when a needle loader enters through the proximal end loading channel 351 and extends through the loading channel support structure 355 and enters into the loading bed portion 370 of the base 310 where a carrier gore 1000 is in a secured position the loading needle enters into the predetermined placement on the gore 1000 based on dosimetry needs for treatment. Once the gore 1000 is loaded it may be trimmed along the trim lines 1259 present on the antipodal surface of the gore 1000 if necessary.

FIG. 7 is a perspective view of a tile carrier 701 when placed in the loading bed 570 of the loading device 500. The lid 520 portion of the loader has been removed so that the tile 701 is visible and one can see that the orientation lines 755 of the tile 701 align directly with the proximal end loading channel 551. Thus, a needle may enter the loader through the proximal end loading channel 551 and extends through the loading channel support structure into the loading bed portion 570 of the base 510 when a carrier tile 701 is in a secured position so that the loading needle enters into the predetermined placement on the tile 701 based on dosimetry needs for treatment. Additionally, with the lid 520 removed one can see that the tile carrier 701 does not extend the full distance to the end of the loader bed 570. In these cases, a specialized lid 520 with a tooth portion 527 can mate with the loader bed 570 and the tooth portion 527 proximity to the shortened tile 701 provides structural support and allows the tile to be more accurately loaded.

Figure 8:
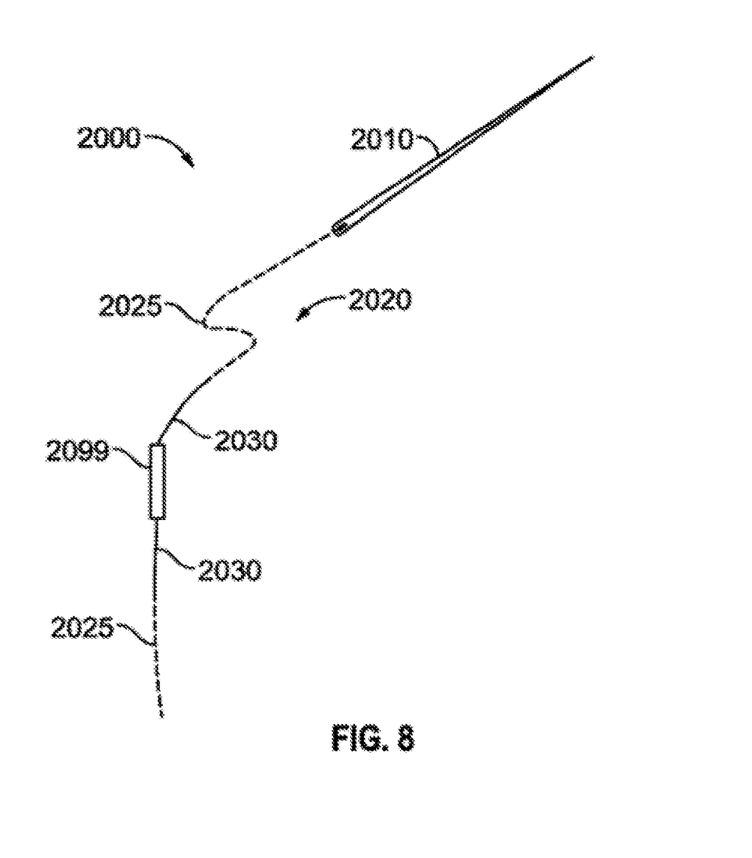
FIG. 8 illustrates a loading apparatus configured to place a radioactive seed in a carrier.

When a needle loading apparatus is used to load the radioactive seeds into the carriers such as that described in FIG. 8, the needle apparatus 2000 feeds through the proximal end loading channel 151 and extends through the loading channel support structure 155 and enters into the loading bed portion 170 of the base 110 where a carrier tile such as 601 (not shown) is in a secured position. The needle apparatus 2000 feeds through the tile carrier 601 and exits out the loading channel exit hole 353. Once the tip of the needle 2010 of the needle apparatus extends through the exit hole 353 the needle 2010 is grasped with a needle-puller and pulled through until the thread 2020 provides a visual determination that the carrier is loaded properly and the seeds are in their proper location. When the seed is placed at the proper depth all of the offset color 2030 (such as purple) disappears inside of the tile 601 and the loader device and the regular color thread 2025 is trimmed away.

Example Transparent Loader Surfaces

As discussed above, in some embodiments a loader may include one or more surfaces (e.g., one or more of the various bases, lids, bedliners, etc.) composed of a transparent material, where transparency is defined to include embodiments with various levels of transparency, from fully transparent to partially transparent. In some embodiments, a level of transparency is determined or selected to provide suitable visibility to a radioactive seed position behind the transparent surface. Thus, depending on the embodiment, the level of transparency required to provide this advantage may vary. For example, if the seed location is detected by human vision, such as by a technician or surgeon that manually handles the loader and monitors position of the seed within the loader, the transparency level may be higher than if the seed location is monitored with a digital detector (e.g., a camera or sensor) that monitors and automatically detects light, whether in the visible or invisible spectrum (e.g., with object detection software executing on a computing device).

In some embodiments, the level of transparency may also be determined or selected to provide suitable shielding of radioactive energy from radioactive seeds or other sources that are placed behind the transparent surface. For example, in some embodiments the transparent material may be impregnated with lead or another material that absorbs or reflects radioactive energy. In embodiments where a human user is handling the loader, the level of radioactive shielding may be increased to reduce radiation absorbed by the user's tissue. Conversely, in a loader system where seeds are inserted into carriers using robotic components, for example, radioactive shielding requirements may be reduced.

Depending on the embodiment, the transparent loader surfaces may be formed of various materials, such as glass, plastic, etc. Such materials may allow shielding objects to be implanted within the material, such as via an injection molding process. Depending on the embodiment, shielding material may be formed above, below, or within a transparent surface of a loader in various manners. For example, in some embodiments a thin layer of high Z foil may be placed above and/or below a transparent surface, such as across an entire area of the transparent surface or a portion of the transparent surface. For example, a suitable shielding level may be obtained by use of a shielding material across the portion of a transparent surface of a loader, while still providing a suitable level of visibility beyond the transparent surface.

Figure 9A:
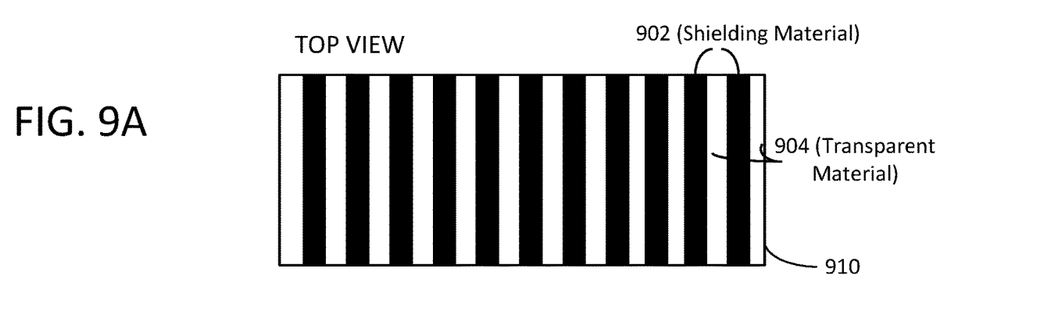
FIGS. 9A, 9B, 9C illustrate various arrangements of shielding material and transparent materials that may be used in various surfaces of the loaders, lids, and/or other structures discussed herein.
Figure 9B:
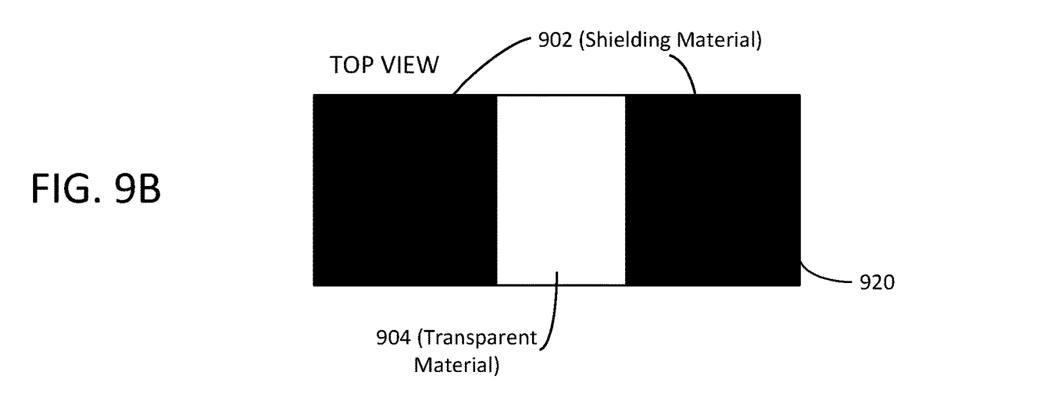
Figure 9C:
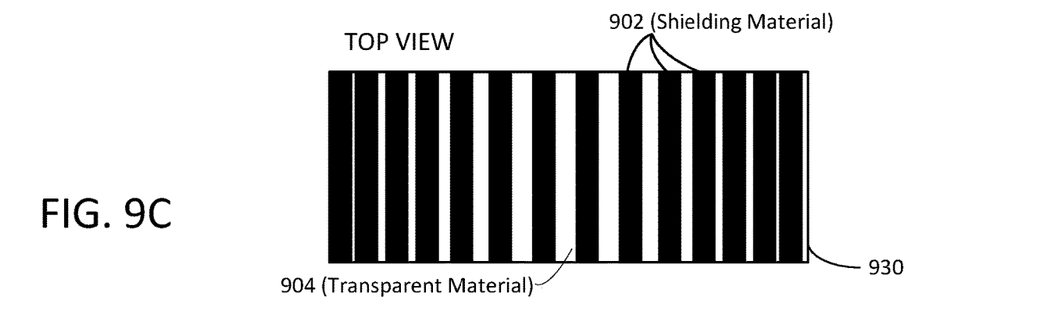

FIGS. 9A, 9B, 9C are top views of arrangements of shielding material and transparent materials that may be used in various surfaces (e.g., surfaces of a loader). In any of these example configurations, the illustrated shielding material may be impregnated within the transparent material (or vice versa) and/or adhered to a top or bottom surface of a transparent material (or vice versa). In other embodiments, the shielding material may be distributed throughout a portion or all of a transparent surface of a loader. In some embodiments, shielding material may also be at least partially transparent, such as having a lower transparency than the transparent material.

In the example of FIG. 9A, the surface 910 includes a plurality of uniformly sized and alternating shielding and transparent sections. In this embodiment, shielding of radiation may be uniformly provided across a length of the surface 910, while also allowing light to pass through the surface 910. In the example of FIG. 9B, the surface 920 includes a central transparent portion surrounded by shielding portions. This configuration may allow visibility into a central portion of a loader, while providing significant radiation shielding on the peripheral portions of the loader. In the example of FIG. 9C, spacing between transparent and shielding materials is increased at a central portion of the surface 930 so that visibility into that central portion is increased, while some radiation shielding is still provided within that central portion, whereas the central portion of surface 920 in FIG. 9B does not include materials specifically for shielding radiation, although even a partially or fully transparent material may be selected based on radiation shielding properties. In other embodiments, any other arrangement of shielding and transparent portions of a loader surface are contemplated. Additionally, loader surfaces that are entirely transparent (e.g., without separate shielding materials) may be used.

Possible advantages associated with use of a transparent loader (including a loader with one or more transparent surfaces) may include, but are not limited to:

- Position of a seed within a loader can be monitored and adjusted while the seed is still being positioned in the loader. Thus, a seed can be more accurately placed within a carrier, such as in a center of a carrier (or other desired location within a carrier). In some embodiments, carriers comprise a material that is at least partially transparent also. Thus, in one embodiment a transparent loader may be used in conjunction with a light source, e.g., a penlight, positioned so that the light passes through a top and bottom surface of the loader (or other surfaces), for example, revealing the position of the carrier within the loader, as well as a seed that may be inserted into the loader and the carrier. Position of a loading tool, such as a needle, may be monitored through transparent surfaces of a loader also.
- A seed that has already been positioned within a carrier may be detected within the carrier and repositioned, if needed. For example, a light may be directed through the loader and carrier to identify position of the seed within the carrier and then monitored as a repositioning device (e.g., a needle, stylus, rod, etc.) is inserted into the loader to reposition the seed.
- May be used to modify a carrier, such as trimming one or more edges of a carrier, with a reduced risk of impacting the one or more seeds embedded therein. For example, a carrier may be trimmed (e.g., using a cutting apparatus to shorten one or more sides) while within the transparent loader and in view of the current position of one or more seeds within the carrier. Other modifications, such as division of the carrier (e.g., separating the carrier into multiple carriers, each with a separate radioactive seed therein) may also more accurately and safely be performed using the various transparent loaders discussed herein.
- Cutting/trimming guides may be embedded, imprinted, etc. or superimposable on the carrier within the transparent loading device.
- May be used to check single seeds, multiple-seed squares or rectangles, gores, dots, or other carriers.
- One or more surfaces of the loader may be marked with an indication of where a seed should be positioned within carriers. For example, a "X" may be printed, engraved, etc. on a top and/or bottom surface of the transparent loader to indicate the ideal position of a seed within the loader. Similar markings may be provided to indicate positions of carriers within the loader.
- May be used with both manual and/or automatic tracking of seed positions within the loaders.
- In some embodiments, such as automated motors, the loader may include only top and/or bottom surfaces (and not include any sides).
- May accommodate pre-made tiles or those made using the loader.
- One or more surface of a loader, e.g., top and/or bottom (or back and/or front), may comprise metal that is manufactured to transmit light by including a series of small holes and/or an array of linear slots.
- A grid pattern of holes in a loader surface, e.g., a back of a metal loader, may secondarily be used to imprint a texture pattern on one side of the carrier so the user can identify front vs back in carriers that contain a seed that is asymmetrically positioned from front to back.
- Separate from manufacturing (positioning a seed within a collagen tile), the back-lighting process described herein can be leveraged for quality assurance by the end user, to verify that seeds have not migrated during shipment, for example.
- In some embodiments, loaded tiles (e.g., "hot" tiles) could be shipped in plastic (or other at least partially transparent material) containers, e.g. transparent front and transparent or translucent back, and these containers could be transilluminated by the end user prior to implantation to confirm that seeds are correctly positioned within the carriers.
- Carriers may be shipped in separate container, such as the containers noted above that are configured for transillumination before and after shipping.
- A container could contain an n×m array of slots that could be filled with hot tiles. These shipping containers may be enclosed in shielding material for shipment.

A loader could also serve as the shipping container. For example, a loader could potentially be pure plastic (completely transparent top, bottom, and/or sides) and then serve as the shipping container sent to the user. Transilluminating the loader during manufacture would allow positioning of seeds prior to shipment, and transilluminating by the end user on receipt could be used for quality assurance to confirm seed position, insertion of additional or different seeds, and/or repositioning of seeds.

The advantages discussed herein are not reliant on the loader providing any particular level of shielding or any shielding at all. For example, in some implementations external shielding around a loader could be provided. For example, a loader may include transparent material in various configurations, without specifically providing radiation shielding (e.g., the transparent materials may inherently provide some minimal level of radiation shielding, but extra shielding materials are not added to the loader specifically for shielding purposes). In one example, such as in the case of a human performing insertion of seeds into carriers in a production environment, the person may be shielded from radiation from the seeds before they are inserted into the loader and from the seeds in the collagen after removal from the loader by, e.g., a shielded workbench with lead glass or a camera/monitor and radiation hand protection.

Although the invention has been described with reference to the above examples, it will be understood that modifications and variations are encompassed within the spirit and scope of the invention.

Other Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof.

What is claimed is:

1. An loading apparatus comprising:
a top surface and a receiving surface; a loading bed configured to support a radioactive seed carrier configured to contain a radioactive seed, wherein the radioactive seed carrier is configured for embedding in a cavity of mammalian tissue; and
a loading channel through the receiving surface, the loading channel configured to receive an injection device, the injection device configured to inject the radioactive seed into the radioactive seed carrier;
wherein the top surface includes one or more transparent portions that allow light to pass therethough and a plurality of radiation shielding portions constructed of a high Z material that provides significant shielding of radiation from the radioactive seed, wherein the plurality of radiation shielding portions are at least partially separated by a corresponding one of the one or more transparent portions, at least one of the one or more transparent portions aligning with a particular portion of the loading bed where the radioactive seed is to be positioned within the radioactive seed carrier.

2. The loading apparatus of claim 1, wherein the portions high Z material is configured to reflect and/or absorb radiation emitted by the radioactive seed.

3. The loading apparatus of claim 1, wherein the one or more transparent portions are translucent.

4. The loading apparatus of claim 1, wherein the at least one of the one or more transparent portions comprise glass or plastic having an opacity of less than 20%.

5. The loading apparatus of claim 1, further comprising:
a bottom surface parallel to the top surface with the receiving surface positioned therebetween.

6. The loading apparatus of claim 5, wherein the bottom surface includes a transparent portion.

7. The loading apparatus of claim 1, wherein the at least one of the one or more transparent portions of the top surface is substantially all of the top surface.

8. A method comprising:
inserting a seed carrier into a loading device having at least a loading bed for supporting the seed carrier and an opposing surface having one or more transparent portions that allow light to pass therethrough and a plurality of radiation shielding portions constructed of a high Z material that provides significant shielding of radiation, wherein at least one of the one or more transparent portions is usable to determine when a radioactive seed is at a desired position in the radioactive seed carrier, wherein the plurality of radiation shielding portions are at least partially separated by a corresponding one of the one or more transparent portions;
moving a loading tool to cause the radioactive seed to move into the seed carrier;
detecting, through the at least one of the one or more transparent portions of the loading device, when the radioactive seed is at the desired position within the radioactive seed carrier; and
in response to detecting the radioactive seed at the desired position within the radioactive seed carrier, withdrawing the loading tool, wherein the seed carrier with the embedded radioactive seed is configured for embedding in a cavity of mammalian tissue.

9. The method of claim 8, wherein the high Z material comprises an element with an atomic number greater than twenty.

10. The method of claim 8, wherein said detecting is performed automatically by an electronic device having one or more optical sensor.

* * * * *

UNITED STATES PATENT AND TRADEMARK OFFICE
CERTIFICATE OF CORRECTION

PATENT NO. : 10,888,710 B1
APPLICATION NO. : 15/824182
DATED : January 12, 2021
INVENTOR(S) : David Brachman et al.

It is certified that error appears in the above-identified patent and that said Letters Patent is hereby corrected as shown below:

On the Title Page

On page 3, in Column 2, item (56), Other Publications, Line 22, delete "fora" and insert --for a--.

On page 3, in Column 2, item (56), Other Publications, Line 48, delete "Millenium." and insert --Millennium.--.

In the Specification

In Column 2, Line 2, delete ""loader")" and insert --"loader").--.

In Column 2, Line 10, delete "a the" and insert --the--.

In Column 11, Line 44, delete "FIG. 9 B" and insert --FIG. 9B--.

In the Claims

In Column 14, Line 10, Claim 1, delete "therethough" and insert --therethrough--.

In Column 14, Line 19, Claim 2, delete "the portions" and insert --the--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*